(12) United States Patent
Palter

(10) Patent No.: US 10,269,457 B2
(45) Date of Patent: Apr. 23, 2019

(54) METHODS AND SYSTEMS FOR PROVIDING AN INTERACTIVE DISCUSSION PLATFORM FOR SCIENTIFIC RESEARCH

(71) Applicant: Steven F. Palter, Sea Cliff, NY (US)

(72) Inventor: Steven F. Palter, Sea Cliff, NY (US)

(*) Notice: Subject to any disclaimer, the term of this patent is extended or adjusted under 35 U.S.C. 154(b) by 308 days.

(21) Appl. No.: 14/251,477

(22) Filed: Apr. 11, 2014

(65) Prior Publication Data

US 2014/0310017 A1   Oct. 16, 2014

Related U.S. Application Data

(60) Provisional application No. 61/811,634, filed on Apr. 12, 2013.

(51) Int. Cl.
| | | |
|---|---|---|
| *G06Q 10/00* | (2012.01) | |
| *G06Q 50/00* | (2012.01) | |
| *G16H 80/00* | (2018.01) | |
| *G06F 19/00* | (2018.01) | |

(52) U.S. Cl.
CPC ............ *G16H 80/00* (2018.01); *G06F 19/00* (2013.01); *G06Q 50/01* (2013.01)

(58) Field of Classification Search
CPC ........................... G06Q 50/22; G06F 19/3425
USPC ......................................................... 705/2, 3
See application file for complete search history.

(56) References Cited

U.S. PATENT DOCUMENTS

| | | | | |
|---|---|---|---|---|
| 8,539,359 B2* | 9/2013 | Rapaport | ............... | G06Q 10/10 |
| | | | | 709/217 |
| 9,432,444 B1* | 8/2016 | Cansino | ............ | G06F 17/30864 |
| 2004/0172405 A1* | 9/2004 | Farran | ................... | G06Q 30/02 |
| 2009/0164438 A1* | 6/2009 | Delacruz | ........... | G06F 17/30011 |
| 2009/0204469 A1* | 8/2009 | Markram | .......... | G06F 17/30722 |
| | | | | 705/326 |
| 2010/0228777 A1* | 9/2010 | Imig | ................. | G06F 17/30699 |
| | | | | 707/772 |
| 2011/0295903 A1 | 12/2011 | Chen | | |

(Continued)

FOREIGN PATENT DOCUMENTS

| | | |
|---|---|---|
| IN | 2886/MUMNP/2015 A | 6/2016 |
| WO | WO1998003923 | 1/1998 |
| WO | WO2014169259 | 10/2014 |

OTHER PUBLICATIONS

International Search Report and Written Opinion of the International Searching Authority dated Sep. 15, 2014 in Patent Cooperation Treaty Application No. PCT/US2014/033879, filed Apr. 11, 2014.

(Continued)

*Primary Examiner* — Hiep V Nguyen
*Assistant Examiner* — Trang T Nguyen
(74) *Attorney, Agent, or Firm* — Carr & Ferrell LLP

(57) ABSTRACT

Provided are computer implemented methods and systems for providing an interactive discussion platform for a scientific research article. According to an example method for providing an interactive discussion platform for a scientific research article, the scientific research article can be received and presented. At least one public medium associated with the scientific research article can be created. An entry related to the scientific research article can be received via the public medium. The entry can include an audio, a video, and a text. Data from the scientific research article and at least one entry can be extracted and analyzed.

22 Claims, 7 Drawing Sheets

(56) References Cited

U.S. PATENT DOCUMENTS

| | | | |
|---|---|---|---|
| 2012/0185478 A1 | 7/2012 | Topham et al. | |
| 2012/0197979 A1* | 8/2012 | Palm | G06O 30/0282 709/203 |
| 2012/0244506 A1* | 9/2012 | Lang | G09B 5/06 434/322 |
| 2013/0080266 A1* | 3/2013 | Molyneux | G06Q 10/00 705/14.72 |

OTHER PUBLICATIONS

Wilson, S. et al. "Video Outreach Journal Club"; Rural and Remote Health, vol. 5, Issue 2, Article 355; May 20, 2005; pp. 1-4.

* cited by examiner

METHODS AND SYSTEMS FOR PROVIDING AN INTERACTIVE DISCUSSION PLATFORM FOR SCIENTIFIC RESEARCH

RELATED APPLICATIONS

The present application claims the benefit of U.S. provisional application No. 61/811,634, titled "Methods and Systems for Providing an Interactive Discussion Platform for Scientific Research," filed on Apr. 12, 2013. The subject matter of the aforementioned application is incorporated herein by reference for all purposes.

FIELD

This application relates generally to data processing and, more specifically, to providing an interactive discussion platform for scientific research and analysis as such.

BACKGROUND

Researchers and scientific and health professionals (including, but not limited to, clinical medical doctors, academics at research universities, medical students, and professionals in the pharmaceutical and medical device industries) have been facing a crisis of exponentially increasing information combined with little time to process this information. Trainees are limited in access to specialists outside their institution and patients are having difficulty identifying experts in their specific fields. Conventional approaches of reviewing new research and publications include conducting meetings and direct communications with representatives of pharmaceutical and medical device companies. However, availability and participation of researchers and scientific and health professionals in local and national meetings, which used to fill the role of guiding the physician through new innovations in the field, are dwindling. Additionally, pharmaceutical and medical device companies have experienced decreased access to physicians, decreased ability to gather real-time market data and lack of access to trainees. New regulations and practice patterns have nearly eliminated direct access to physicians and have completely prohibited discussions of off-label use of medications. Thus, health professionals have to review large volumes of publications to find the information they need.

SUMMARY

Provided are computer-implemented methods and systems for providing an interactive discussion platform for scientific research articles (including medical articles, academic papers, patents and patent publications and the like). This interactive discussion platform serves as a collaborative mechanism for finding scientific knowledge and information from peers using scientific research articles as a foundation for conversations between the peers, as well as for patients and researchers to find specialists. The interactive discussion platform also provides the ability to mine data from these conversations, as well as the ability to analyze the data that is mined. Furthermore, the interactive discussion platform may provide a link to a particular scientific research article and/or reference the article's content, an online discussion forum (audio and/or video) associated with that article, as well as access to the raw data of the conversations that are taking place in connection with the linked article.

Also provided are methods and systems for providing an interactive discussion platform for a scientific research article. The system for providing an interactive discussion platform for a scientific research article can include a processor and a database in communication with the processor. The processor can be configured to receive a scientific research article and present the scientific research article online. The processor can further be configured to create a public medium for discussion associated with the scientific research article. One or more entries (e.g., an audio, a video, and a text) related to the scientific research article can be received from one or more users via the public medium. The entries can be accessed once or multiple times. The entries can also be accessed at the user's chosen pace. By providing the entries, users can take part in discussion of the scientific research article, express their opinion about the scientific research article, and provide additional information related to the scientific research article. A processor can extract data from the scientific research article and the entries associated with the scientific research article and analyze the data using natural language processing, manual analysis, big data analytics, and keyword analysis. The analysis can provide information to practitioners to solve clinical problems, create collaborations between health and scientific professionals and researchers, provide patients with access to specialists, provide trainees a connection with specialists and mentors, reveal various concerns, sentinel events, market trends, reactions to marketing messages and product launches, and other feedback associated with the scientific research article.

Provided also is a computer-implemented method for providing an interactive discussion platform for a scientific research article. According to the method, the scientific research article can be received and presented. A public medium for discussion associated with the scientific research article can be created. An entry (e.g., an audio, a video, and a text) related to the scientific research article can be received via the public medium as well as other entries from further users, thereby enabling interactive discussion of the scientific research article. A processor can extract data from the scientific research article and the entries associated with the scientific research article and analyze the data using natural language processing, manual analysis, and keyword analysis. The analysis can reveal concerns, sentinel events, market trends, reactions to marketing messages and product launches, and other feedback associated with the scientific research article.

Provided also is a machine-readable medium involving instructions, which when implemented by one or more processors, perform various operations including receiving a scientific research article and presenting the scientific research article. A public medium for discussion associated with the scientific research article can be created. An entry (e.g., an audio, a video, and a text) related to the scientific research article can be received via the public medium as along with other entries from further users, thereby enabling interactive discussion of the scientific research article. In addition, public information about a presented research article can be accessed, topics (as well as authors, journals, fields, subject matter, etc.) of the article can be identified, the identified information can be aggregated by author, journal, or topic, a summary of the aggregated information can be presented, and interactive discussion and/or analysis can be provided regarding the aggregated information. Trends in research (including user trends with regard to the interactive discussion) in the aggregated content can also be analyzed. A processor can extract data from the scientific research article and the entries associated with the scientific research article and analyze the data using natural language processing, manual analysis, and keyword analysis.

BRIEF DESCRIPTION OF DRAWINGS

Exemplary embodiments are illustrated by way of example and not limitation in the figures of the accompanying drawings, in which like references indicate similar elements.

DETAILED DESCRIPTION

Figure 1:
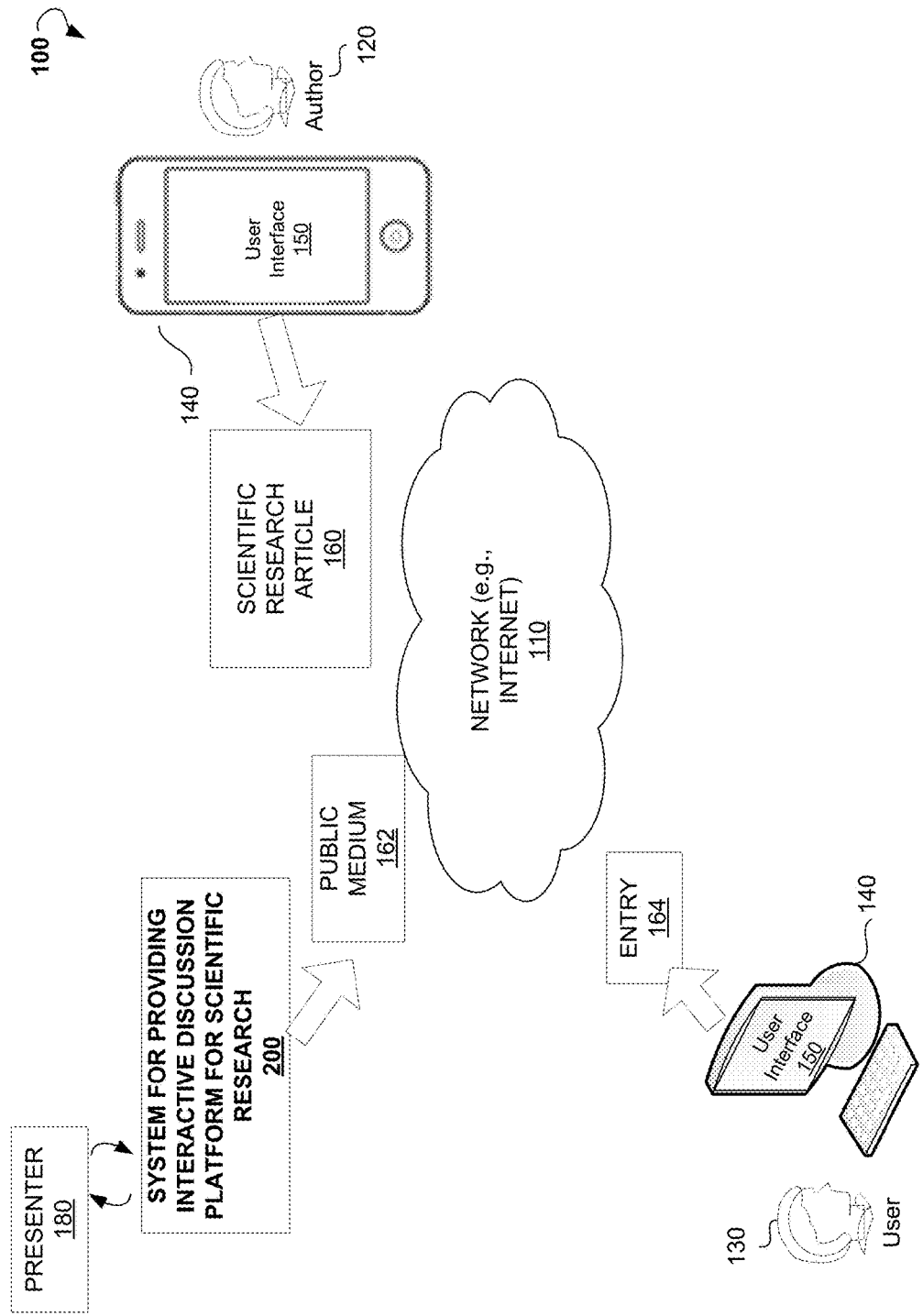
FIG. 1 illustrates an example environment within which the systems and methods for providing an interactive discussion platform for a scientific research article may be implemented.

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.

Various computer implemented systems and methods for providing an interactive discussion platform for a scientific research article are described herein. Large volumes of information related to research and various technologies in a medical area pose a problem of timely processing and implementing for medical staff, trainees, researchers, and patients. The described systems and methods provide a solution to the problem affecting the world of medical and scientific research, practice, marketing, providing information to regulatory bodies, providing information to organization for needs-assessment of members, continuing medical education, examination, and credentialing, and the like. Using the systems and methods for providing an interactive discussion platform for a scientific research article disclosed herein, scientific journals and societies can transform their static literature into dynamic forums that connect physicians with each other. Pharmaceutical and medical device companies can access real-time and real-world marketing data unavailable elsewhere.

Scientific research articles published in scientific journals and other resources can be provided online, in whole or in part, via public resources. Readers of the scientific research articles can be provided with a public medium to leave feedback concerning the scientific research article and receive scientific knowledge and information from their peers using the research articles as a foundation for the conversations. The public medium can include a discussion forum, online video journal club (an online meeting between at least two communities of individuals or within one community of individuals in which at least one scientific research paper is discussed to determine implementations of the research, shortcomings and value of the research, etc.), video article, online poll, and interactive online portal. The public medium can facilitate an efficient discussion of the scientific research article. Moreover, the presenter and/or the author can also participate in the discussion to clarify contents of the scientific research article and provide additional data. The public nature of the media provides for interactive conversations related to the scientific research article and involving a wide audience. Researchers and practitioners can join as a single scientific community.

Data from the entries associated with the public medium as well as the scientific research article can be extracted, culled, and analyzed using natural language processing, manual analysis, or keyword analysis. These analytic techniques can be directed to key words or phrases in order to identify trends, competitive products, positive and negative events, phrases, and messages. The analysis can simplify data mining (and/or provide trend information) for the readers and provide feedback to the interested parties. Based on the analysis of the interactive discussion, feedback received from researchers and practitioners can be evaluated, market trends and reactions can be determined, and product use information can be ascertained.

Additionally, based on the analysis of the interactive discussion, a value of the scientific research article can be determined. In various embodiments, the value is associated with the popularity of the scientific research article, evaluation of the scientific research article, marketing opportunities related to the scientific research article, and so forth. Additionally, the presenter or a user can receive immediate response to his scientific research article and general development points associated with the scientific research article.

Using the system for providing an interactive discussion platform for a scientific research article, a printed publication can transform its static database of journal articles into a live, interactive social network, and can change how scientific research is presented. The researchers and practitioners who participate in individual journal clubs can develop new connections and learn about innovations in real time. Patients can find specialists related to a medical problem, researchers can find collaborators, and trainees can find mentors and specialists. Students can find mentors through an online network. The medical industry can obtain a new window into the best industry practices facilitated by the discussion of healthcare innovations by researchers and healthcare professionals.

Referring now to the drawings, FIG. 1 illustrates an environment 100 within which the systems and methods for providing an interactive discussion platform for a scientific research article may be implemented. The environment 100 shows a system 200 for providing an interactive discussion platform for a scientific research article, a network 110, an author 120, a user 130, client devices 140, and a presenter 180.

The network 110 may include the Internet or any other network capable of communicating data between devices. Suitable networks may include or interface with any one or more of, for instance, a local intranet, a PAN (Personal Area Network), a LAN (Local Area Network), a WAN (Wide Area Network), a MAN (Metropolitan Area Network), a virtual private network (VPN), a storage area network (SAN), a frame relay connection, an Advanced Intelligent Network (AIN) connection, a synchronous optical network (SONET) connection, a digital T1, T3, E1 or E3 line, Digital Data Service (DDS) connection, DSL (Digital Subscriber Line) connection, an Ethernet connection, an ISDN (Integrated Services Digital Network) line, a dial-up port such as a V.90, V.34 or V.34bis analog modem connection, a cable modem, an ATM (Asynchronous Transfer Mode) connection, or an FDDI (Fiber Distributed Data Interface) or CDDI (Copper Distributed Data Interface) connection. Furthermore, communications may also include links to any of a variety of wireless networks, including WAP (Wireless Application Protocol), GPRS (General Packet Radio Service), GSM (Global System for Mobile Communication), CDMA (Code Division Multiple Access) or TDMA (Time Division Multiple Access), cellular phone networks, GPS (Global Positioning System), CDPD (cellular digital packet data), RIM (Research in Motion, Limited) duplex paging network, Bluetooth radio, or an IEEE 802.11-based radio frequency network. The network 110 can further include or interface with any one or more of an RS-232 serial connection, an IEEE-1394 (Firewire) connection, a Fiber Channel connection, an IrDA (infrared) port, a SCSI (Small Computer Systems Interface) connection, a USB (Universal Serial Bus) connection or other wired or wireless, digital or analog interface or connection, mesh or Digi® networking. The network 110 can be a network of data processing nodes that are interconnected for the purpose of data communication.

The system 200 for providing an interactive discussion platform for a scientific research article can include a user interface 150 that can be displayed by any of the client devices 140. The system 200 for providing an interactive discussion platform for a scientific research article can be cloud-based and reside on a cloud-based server, reside on a server of the presenter 180, or on dedicated servers of the system 200. The presenter 180 can include a journal, a premier research university, a practitioner, and so forth. The client device 140 can include any computing device, such as a mobile device, a tablet personal computer (PC), a laptop, a desktop computer, and so forth. The client device 140, in some exemplary embodiments, includes a Graphical User Interface (GUI) for displaying the user interface 150. In a typical GUI, instead of offering only text menus or requiring typed commands, the system presents graphical icons, visual indicators, or special graphical elements called widgets that can be utilized to allow the author 120 or the user 130 to interact with the user interface 150. The client device 140 can be configured to utilize icons used in conjunction with text, labels, or text navigation to fully represent the information and actions available to users.

The author 120 can provide the scientific research article 160 to the system 200 for providing an interactive discussion platform for a scientific research article or to the presenter 180 associated with the system 200. The presenter can provide, to the system 200, the scientific research article 160 for presenting on an online resource, such as a discussion forum or a journal club. The scientific research article 160 can be received as part of a publication process, or it can be retrieved by crawling a database. The scientific research article 160 can include a medical article. The presenter can provide for online presentation the scientific research article 160 published in the printed publication or articles rejected from the main journal. In the latter case, the author may agree to alternative publication options. In the online resource, the scientific research article 160 can be presented in whole or in part. For example, the online-presented part of the scientific research article can include an author list, affiliations, keywords, title, abstract, capsule or a subset of content, and so forth.

For the presented article, the system 200 can create a public medium 162 for discussion of the scientific research article 160. In various embodiments, the public medium 162 includes a discussion forum, a journal club, a poll, a chat, and so forth. The user 130 can access the scientific research article 160 presented by the system 200 and provide an entry 164 with his feedback to the scientific research article using the public medium 162. The entry nature may depend on the public medium 162; thus, for the discussion forum, it can be a text comment, while for a journal club it can be a video record or an online video or audio conference, and so forth. The entry 164 can reflect a point of view of the user 130 concerning the scientific research article 160, raise accompanying problems, provide assessment of the scientific research article 160 by the user 130, and the like. The entry 164 can be available to users who can provide entries associated with the scientific research article 160. Therefore, the system 200 can facilitate interactive discussion using the public medium 162 as a collaborative mechanism for finding scientific knowledge and information from peers using the scientific research article 160 as a foundation.

At one or more times in the publication process, the author 120 can be solicited to participate in the online discussion of the scientific research article 160. This can include opting in to email notifications or formal agreements to participate in discussion. This can occur upon submission or upon acceptance or other time points.

Content of the scientific research article 160 and one or more entries 164 can be analyzed via keyword analysis and natural language processing of the content. Additionally, the content of the scientific research article 160 can be identified by manual reading and categorization. Thus, readers can easily retrieve information and navigate the system 200.

Moreover, based on the analysis of the interactive discussion, as well as the access (e.g. number of users reading and/or discussing the article), popularity (e.g., number of users commenting on the article), and ranking of the article, the system 200 can determine a value of the scientific research article 160. The value can be associated with the interest of the audience to the scientific research article 160, their evaluation, and so forth.

Online discussion and conferencing opportunities create an interactive social network devoted to inventions and development in the scientific and medical area. The system 200 connects practitioners, researchers, and students in a virtual community that facilitates collaborations and networking for employment and research opportunities and also provides topic-based access to specialists. Practitioners using the system 200 get the latest innovations in their field in a fraction of the time it would take to travel to a conference. They have direct access to thought leaders in their field sharing the information they need. Researchers and their universities connect with other innovators, and also connect in real time to practitioners who will make use of their discoveries.

The system 200 for providing an interactive discussion platform for a scientific research article can be an open source, with open access, and free and available to clinical practitioners, researchers, and students.

Figure 2:
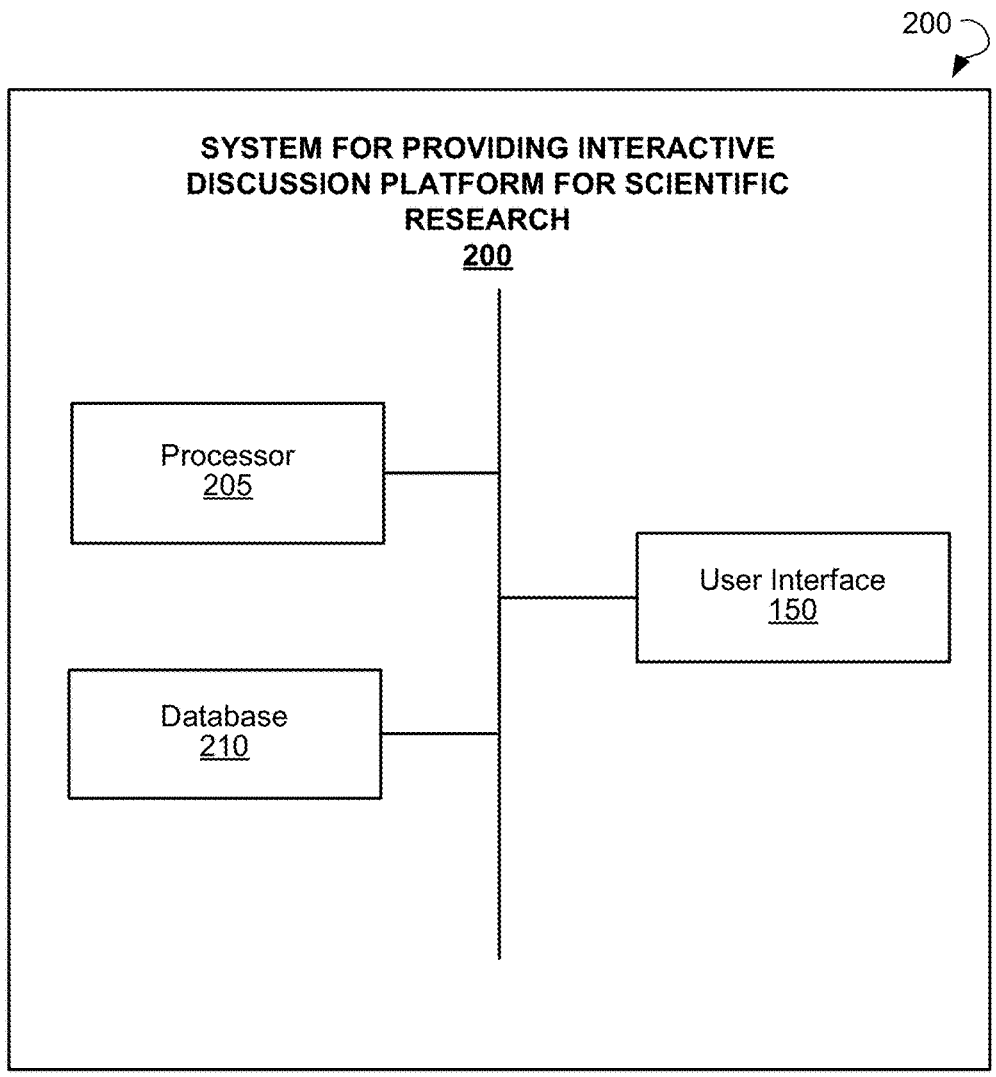
FIG. 2 is a block diagram showing modules of a system for providing an interactive discussion platform for a scientific research article, in accordance with certain embodiments.

FIG. 2 is a block diagram showing modules of a system 200 for providing an interactive discussion platform for a scientific research article, in accordance with certain embodiments. Specifically, the system 200 for providing an interactive discussion platform for a scientific research article can include a processor 205, a database 210, and user interface 150. The processor 205 can include a programmable processor, such as a microcontroller, central processing unit (CPU), and so forth. In other embodiments, the processor 205 may include an application-specific integrated circuit (ASIC) or programmable logic array (PLA), such as a field programmable gate array (FPGA), designed to implement the functions performed by the system 200. The processor 205 may be configured to receive a scientific research article from a presenter or from an author. Alternatively, information from the printed journal article to be presented using the system 200 can be identified via publicly accessible links to that content. This can be search engines, online citations, or the journal online listings either of itself or a clearinghouse aggregator from the presenter or society. This content can be manually copied or the sites can be crawled using a web crawler or a scraper to retrieve desired content. Using this approach, authors can be contacted for participation after the scientific research article is presented. The authors can be identified using, for example, contact information associated with the article.

In some embodiments, a username and password can be automatically or manually generated for the author who submits papers, whose article is accepted for publication, or who opts in. Agreement to participate in online discussion can be made a requirement for publication. The generation of user name and password can be automatic or manual. This step integrates participation in discussion with submission of the manuscript for traditional publication. The processor 205 can further be configured to present the scientific research article and create one or more public mediums for the scientific research article. When the scientific research article is accepted for presenting or for publication, a unique page or post for it can be created. This can be done manually or automatically. A link to the presented scientific research article can be sent to the author.

In some embodiments, a link for discussion of the scientific research article is embedded into either the abstract of the article, the title page of the printed article, or a QR or other similar graphical link on the printed article and/or table of contents of the journal next to the article listing. Thus, audience of the printed publication can easily access online resources and take part in the discussion of the article.

The processor 205 can receive at least one entry related to the scientific research article via the public medium. Notification about the feedback received in relation to the scientific research article can be sent to the author. Other users and the author can access the entry and provide additional entries related to the scientific research article in real time. The entries can provide valuable information from peer researchers, practitioners, and patients. The processor 205 can extract data from the entries and the scientific research article to analyze and determine user preferences, actual use of drugs and devices, market trends, and so forth. Geographic targeting can allow companies to adjust direct sales actions. Impact and design of tertiary use can be transformed while rapid reactions from the marketplace are monitored. Furthermore, off-label use can be freely discussed by end user physicians and the discussion can be analyzed.

Additionally, the entry can be indicative of the value of the presented article, so the processor can process the entry to determine the value of the scientific research article. Furthermore, users can be allowed to vote on the value of the entry. User feedback concerning the value can be provided to users of the system 200. In some embodiments, entries can be sorted according to their value.

The database 210 can be configured to store at least the scientific research article and one or more entries. Additionally, the author can be invited or required to submit raw data associated with the scientific research article. The raw data received from the author can also be stored in the database 210 and a mechanism for access by other users can be established. Collaborative research can be conducted with this dataset and authorship can be shared between those providing original data and the final users.

In some embodiments, the system 200 can also include the user interface 150 configured to enable interaction between the system 200 and users.

Figure 3:
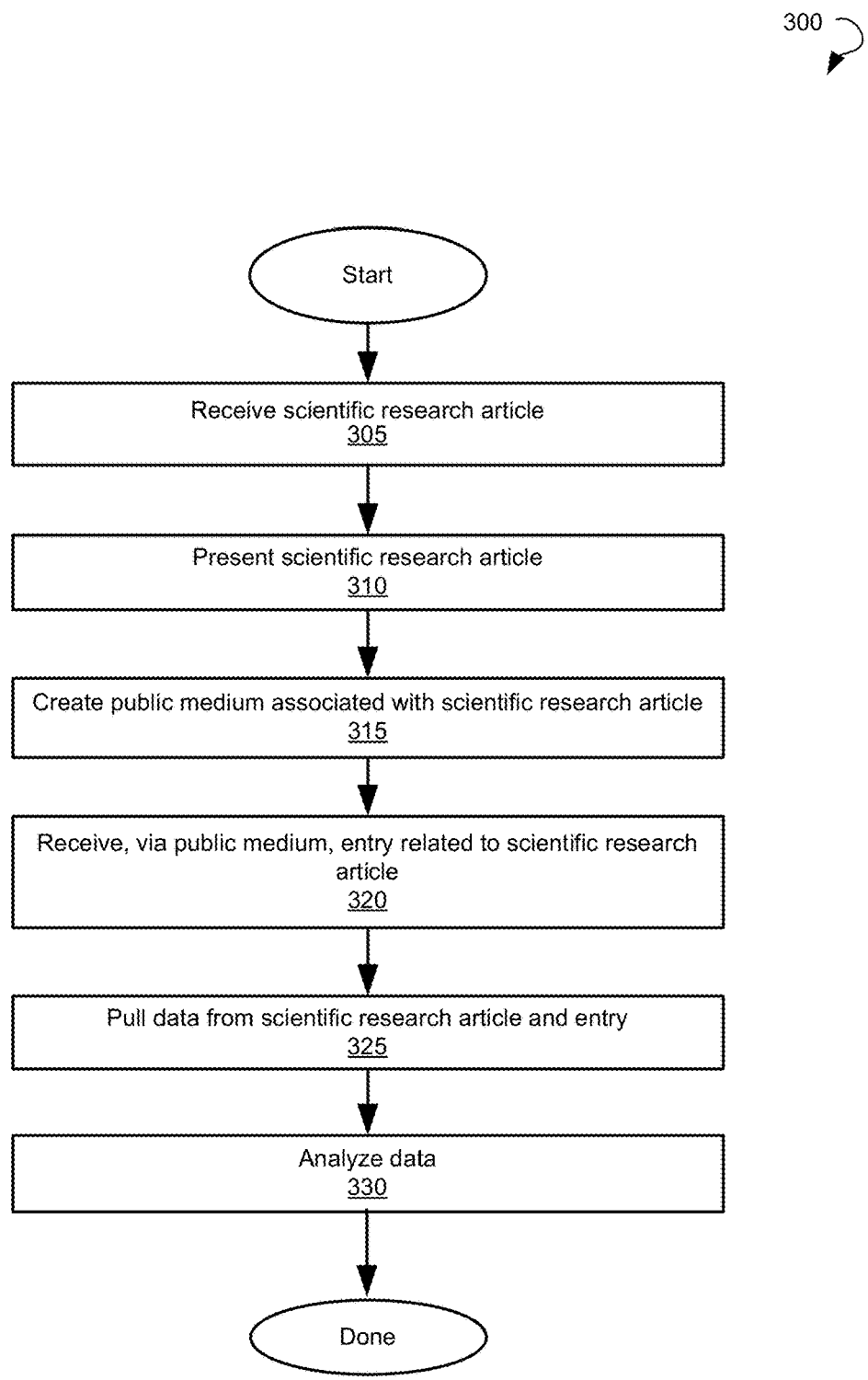
FIG. 3 is a flow chart illustrating a method for providing an interactive discussion platform for a scientific research article, in accordance with some example embodiments.

FIG. 3 is a flow chart illustrating a method 300 for providing an interactive discussion platform for a scientific research article, in accordance with certain embodiments. The method 300 can be performed by logic that may comprise hardware (e.g., dedicated logic, programmable logic, and microcode), software (such as software run on a general-purpose computer system or a dedicated machine), or a combination of both. In one example embodiment, the processing logic resides at the system 200 for providing an interactive discussion platform for a scientific research article, and the various elements of the system 200 can perform the method 300. It will be appreciated by one of ordinary skill that examples of the foregoing modules may be virtual, and instructions said to be executed by a module may, in fact, be retrieved and executed by software. Although various elements may be configured to perform some or all of the various operations described herein, fewer or more elements may be provided and still fall within the scope of various embodiments.

As shown in FIG. 3, the method 300 may commence at operation 305 with receiving a scientific research article by the system 200. The scientific research article can be provided by a presenter, an author of the scientific research article, or retrieved by the system 200 from publicly accessible information.

At operation 310, the scientific research article is presented on an online resource, such as a web site or portal. Additionally, content of the scientific research article can be identified via keyword analysis, natural language processing of the content, or manual reading and categorization. According to the identification, a taxonomy of article content genres can be created. Readers of the journal, authors, or users can be identified and traced based upon the taxonomy system. Each of them can be associated with one or more specific areas and, optionally, assigned a level of expertise in that area. Additionally, the readers, authors, and users can be identified based upon surveys sent or voting articles associated with the articles.

At operation 315, at least one public medium associated with the scientific research article can be created. The public medium for the medical article includes a discussion page on a discussion forum, a journal club discussion, a poll, a chat, and so forth.

Since multiple public media can be created for the same medical article, the public media can cross-reference each other. Additionally, public media of the scientific research articles related to similar topics can reference each other. Moreover, when the system 200 is associated with multiple presenters, scientific research articles associated with different presenters can reference each other. The content can be aggregated and can be provided for discussion based on topic across journals and/or within journals, and trends in the topics can be analyzed.

At operation 320, at least one entry related to the scientific research article can be received from the user. The user includes a reviewer, an author, an editor, a peer of the author, a researcher, a patient, and so forth. The entry can be in a text, an audio, a video, a picture, an answer to the poll, and so forth. In some embodiments, the entry is related to a conference or a meeting associated with the scientific research article. A discussant or a group of discussants can be at a live event and can present the discussion at the event or stream it for viewing or participation by those at the live event. Users can discuss scientific research, receive further scientific knowledge, and information from peers using various public media. Thus, readers can become part of ongoing, dynamic, live discussion that enhances the value of the original research. The readers can obtain a direct access to leading experts in the field and the ability to be mentored by experts from around the world and develop collaborations for new projects.

At operation 325, data from the scientific research article can be extracted. Text associated with comments, discussions from video conferences, posts on social networks related to the scientific research article can be collected and analyzed at operation 330. The analysis can cull reactions and market information from users and determine market trends. In addition, the analysis can further be made to determine trends from what is being discussed and accessed on the platform. The analysis can be performed using various approaches such as, for example, natural language processing, manual analysis, keyword analysis, and so forth. The analysis can target key words or phrases to identify trends, competitive products, or sentinel positive and negative events or phrases and messages from marketing. Analytic reports of products, devices, procedures, or competitive products and devices or hot topics can be provided to industry regulators, educational groups, and the like.

The system 200 can actively learn topics of interest based on what the users read or present and determine topics popular with all users, in specific user groups, or for a particular user. Accordingly, the system 200 can send periodic updates of top discussions or new discussions in areas of particular interest of the user or unrelated areas the user might like based on algorithms.

In some example embodiments, value of the scientific research article can be determined. The determined value can be provided to the users and/or the author, and optionally, to a third party, such as a medical company. Based on the value, popularity of the scientific research article can be ascertained, and the scientific research article can be assigned a rating in relation to other scientific research articles. The rating enables detecting of top scientific research articles, top areas, and so forth.

In some embodiments, the method 300 includes creating a social network where the users of the system 200 are social network members. To provide the entry associated with the scientific research article, the user may need to be a social network member. Membership can be both open or require an invitation from the social network member.

Figure 4:
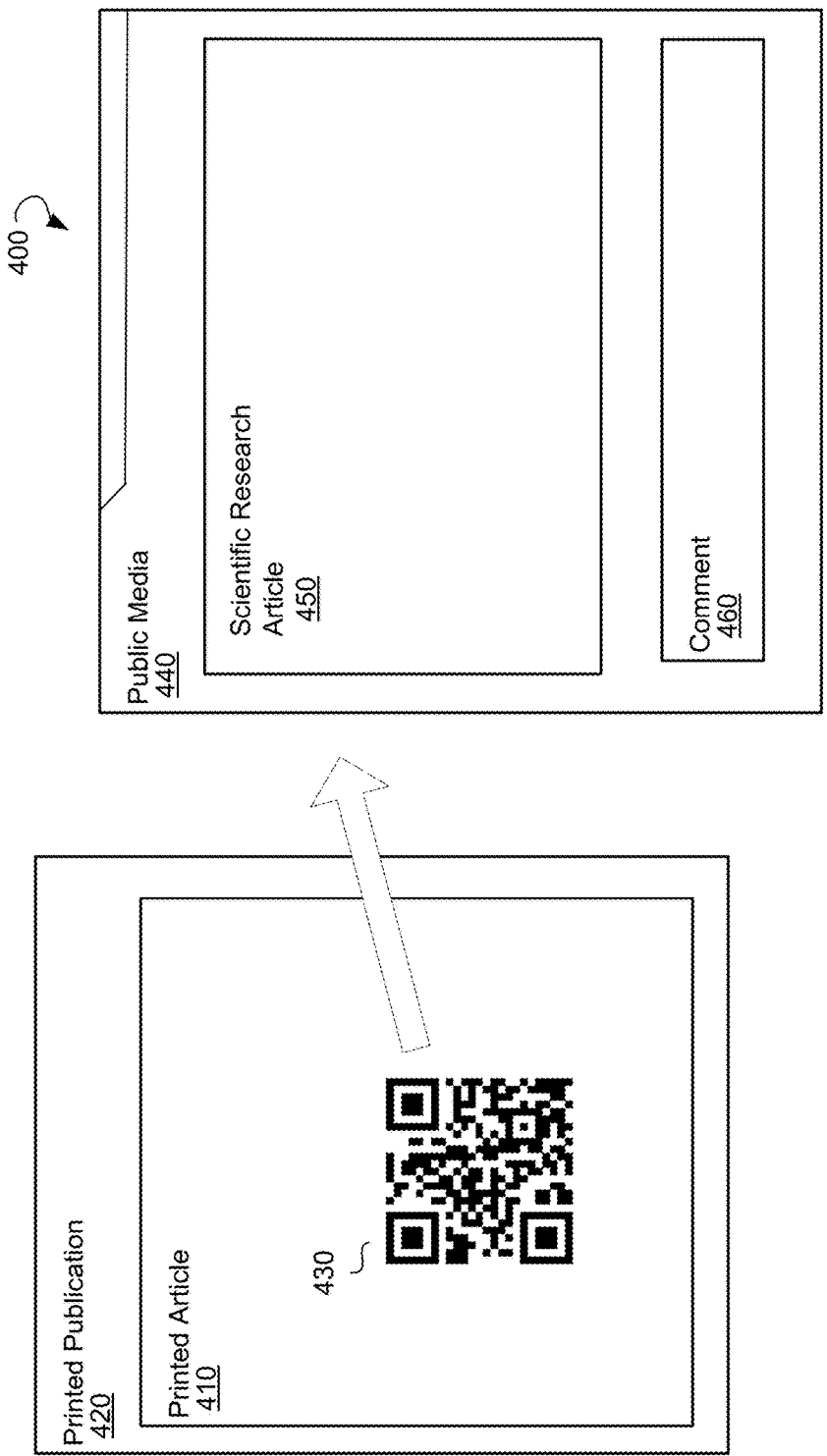
FIG. 4 represents accessing a scientific research article by scanning a Quick Response (QR) code, in accordance with some example embodiment.

FIG. 4 represents accessing 400 a scientific research article by scanning a QR code, in accordance with an example embodiment. A printed article 410 in the printed publication 420 of the presenter can include a link to a scientific research article 450 (e.g., a medical article) associated with the printed article 410. In some embodiments, the link includes a QR code 430 to easily access the scientific research article. The user can scan the QR code 430 using, for example, a smartphone. Upon scanning, a public media 440 providing the scientific research article 450 can be displayed on a screen of the smartphone. The user can read one or more comments 460 related to the scientific research article 450, provide his or her comment, and see related scientific research articles and/or public media.

Figure 5:
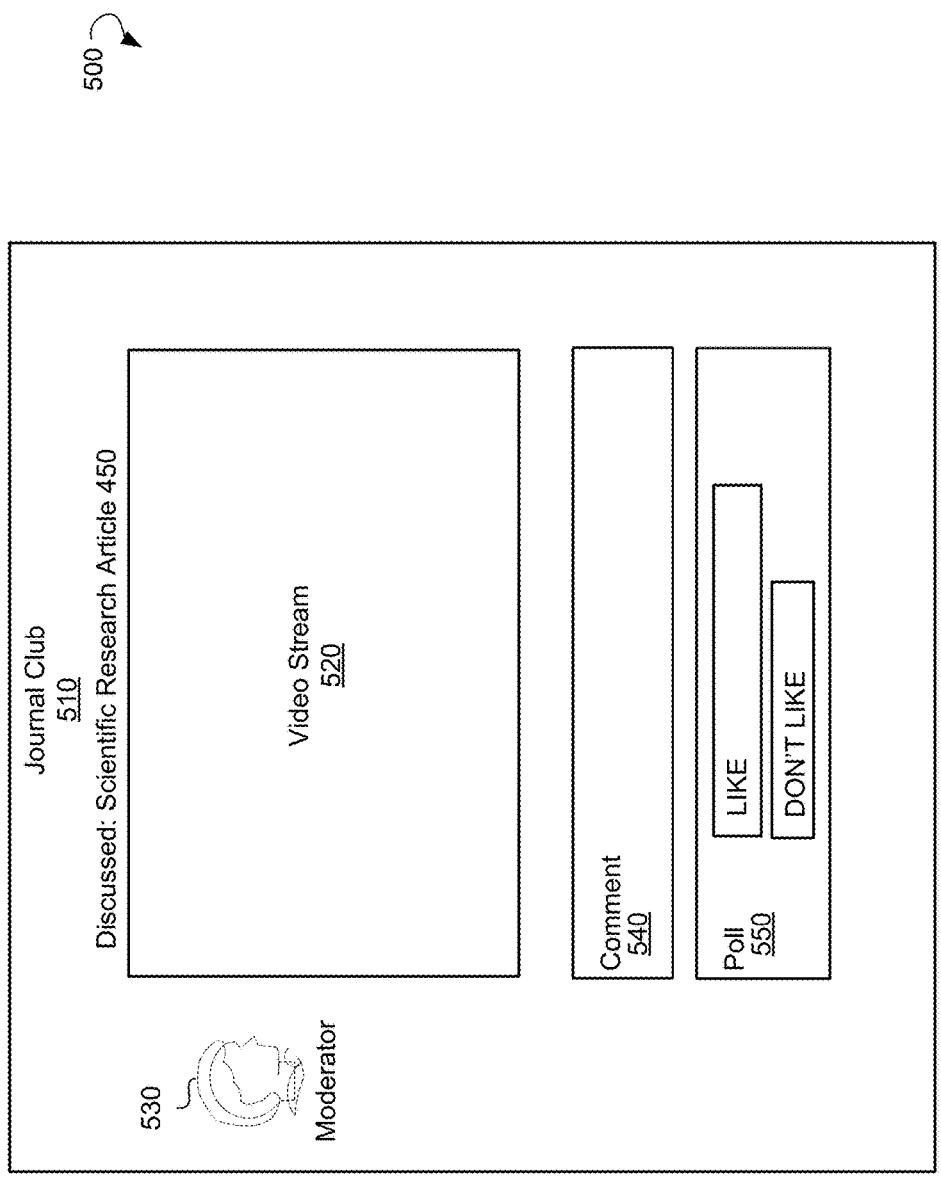
FIG. 5 represents a journal club meeting page, in accordance with some example embodiments.

FIG. 5 represents a journal club meeting 500, in accordance with an example embodiment. A journal club 510 can provide and organize an event, such as demonstrating a video recording, a virtual conference, and other multimedia materials related to a scientific research article. The journal club 510 can announce an upcoming event to the audience (for example, to the users of the system 200 or to a wider audience). A public interface helps participants and audience alike find out all the details about the upcoming event, make connections before the event, and get publicity out about the event.

A scientific research article, for example, the scientific research article 450, can be chosen for discussion by an editor or an editorial board or via social voting (e.g. in the social network associated with the system 200). The scientific research article 450 to be discussed at the event can be one or more than one article related by a topic and could include original new publications and/or classical references related to that topic. The author of the scientific research article 450 and/or a group of discussants can be solicited to participate in the event via online advertising, email, or printed invitations. In some embodiments, the event is led by a moderator 530.

In an example embodiment, a concierge helps all panel members set up for the video event, integrate with the technological platform, and helps with all practical needs. The concierge gives the panelists all of the data and articles in advance so that they are fully prepared for the live event. They also give training to student presenters on how to maximize their participation and educate them about a medical conference experience. In some situations, cameras and microphones are sent ahead of time and participants are assisted with set-up.

Registration to the event can be open or require login in registration and can be free or paid. The users who register in advance or on mailing lists can be sent invitations or reminders via email or text message. Post event messages including replay links can be sent to the same groups.

When the event is live, a video stream 520 of the event can be provided to the users, and the video steam can be controlled by the moderator (or producer) 530 who switches camera focus on each speaker or it can be automatic based on who is speaking.

Polls 550, chats (not shown), and comments 540 can occur in real time with the live event (via online web interface, or text message based or smart phone based). In some embodiments, the polls 550, chats, and comments 540 are coordinated by the backstage team. Access to the comments 540, polls 550, and so forth can be public or private and could be shared with participants.

The entire event can be replayed or submitted for publication as a video article. Content of the event, as well as discussions and the like associated with the event, can be analyzed.

An individual user associated with the group video chat can be replaced by a group of users which can be at live event. The camera for a group video chat can be either a wide angle camera, a mobile camera controlled by a cameraman, or a remote controlled camera with pan tilt zoom capability (PTZ). In case of PTZ, it can be controlled by a participant in the room with a remote control, a device passed from speaker to speaker which the camera follows, or remotely controlled over Internet Protocol (IP) by a controller operator in another location.

Figure 6:
FIG. 6 shows an example journal club page, in accordance with some example embodiments.

FIG. 6 shows an example journal club page 600. The journal club page 600 can include a video stream 610 associated with a video conference for the scientific research article. The video stream 610 can include video feeds from a plurality of participants. The video stream 610 can be demonstrated live or as a recording.

Participants of the video conference can critique and analyze the scientific research article. The journal club page 600 can bring the discussion of the participants to a wide audience by leveraging video conference and chat technologies. The author of the scientific research article can be a participant of the video conference to answer questions and lend additional insight. Additionally, participants and/or other users can post comments 620 related to the scientific research article, video discussions of the scientific research article, and so forth. Discussions during the video conference, comments 620, votes, and other information related to the scientific research article can be retrieved and analyzed to determine audience feedback to the scientific research article and to reveal additional information provided by the participants and/or other users.

Figure 7:
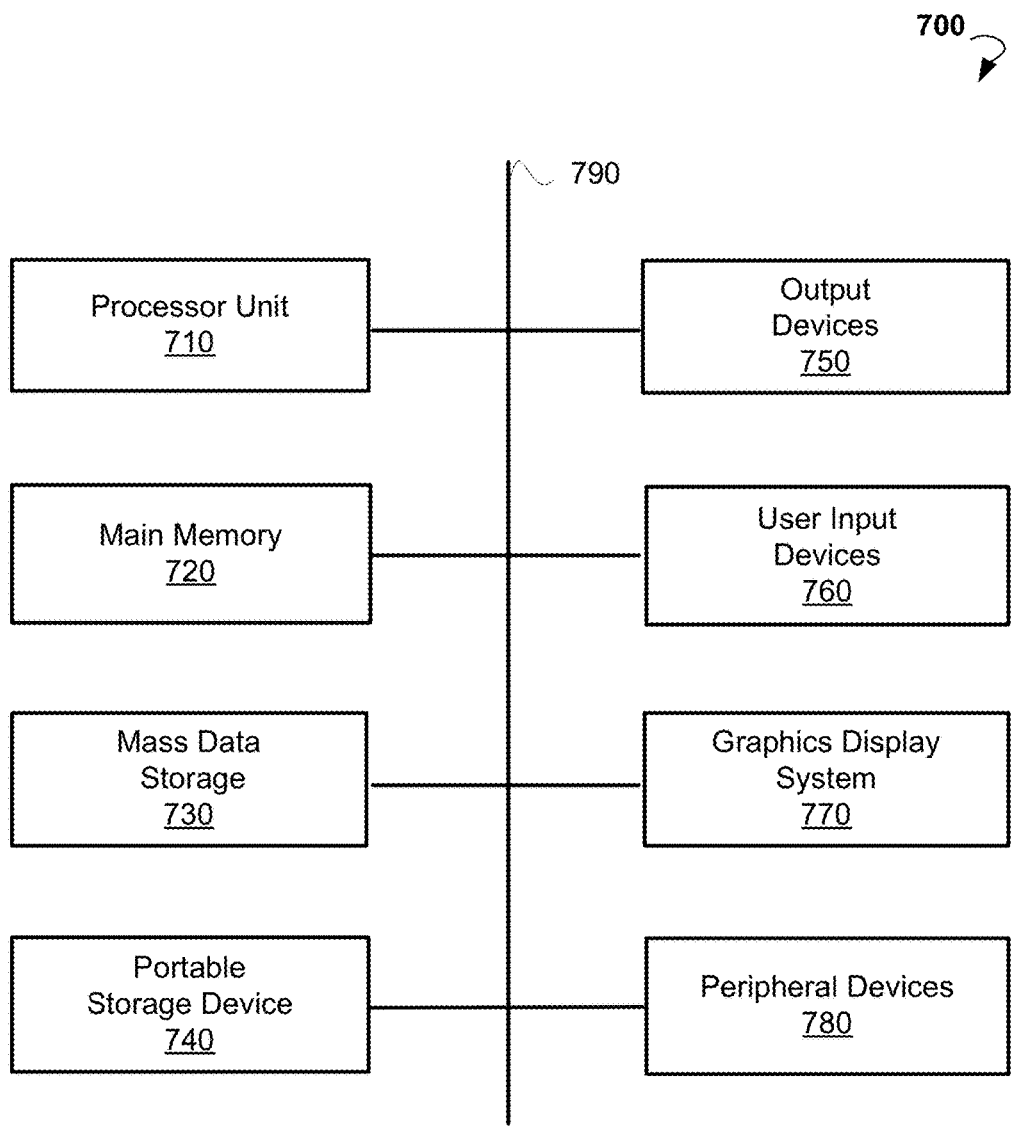
FIG. 7 shows a diagrammatic representation of a computer system or a machine, within which a set of instructions for causing the machine to perform any one or more of the methodologies discussed herein, can be executed.

FIG. 7 shows a diagrammatic representation of a computer system or a machine, within which a set of instructions for causing the machine to perform any one or more of the methodologies discussed herein, can be executed. The system 700 of FIG. 7 can be implemented in the contexts of the likes of computing systems, networks, servers, or combinations thereof. The computing system 700 of FIG. 7 includes one or more processor units 710 and main memory 720. Main memory 720 stores, in part, instructions and data for execution by processor 710. Main memory 720 stores the executable code when in operation. The computer system 700 of FIG. 7 further includes a mass data storage 730, portable storage device 740, output devices 750, user input devices 760, a graphics display system 770, and peripheral devices 780. The methods may be implemented in software that is cloud-based.

The components shown in FIG. 7 are depicted as being connected via a single bus 790. The components may be connected through one or more data transport means. Processor unit 710 and main memory 720 are connected via a local microprocessor bus, and the mass data storage 730, peripheral device(s) 780, portable storage device 740, and graphics display system 770 are connected via one or more input/output (I/O) buses.

Mass data storage 730, which can be implemented with a magnetic disk drive, solid state drive, or an optical disk drive, is a non-volatile storage device for storing data and instructions for use by processor unit 710. Mass data storage 730 stores the system software for implementing embodiments of the present disclosure for purposes of loading that software into main memory 720.

Portable storage device 740 operates in conjunction with a portable non-volatile storage medium, such as a floppy disk, compact disk (CD), digital video disc (DVD), or USB storage device, to input and output data and code to and from the computer system 700 of FIG. 7. The system software for implementing embodiments of the present disclosure is stored on such a portable medium and input to the computer system 700 via the portable storage device 740.

User input devices 760 provide a portion of a user interface. User input devices 760 include one or more microphones, an alphanumeric keypad, such as a keyboard, for inputting alphanumeric and other information, or a pointing device, such as a mouse, a trackball, stylus, or cursor direction keys. User input devices 760 can also include a touchscreen. Additionally, the computer system 700 as shown in FIG. 7 includes output devices 750. Suitable output devices include speakers, printers, network interfaces, and monitors.

Graphics display system 770 include a liquid crystal display (LCD) or other suitable display device. Graphics display system 770 receives textual and graphical information and processes the information for output to the display device.

Peripheral devices 780 may include any type of computer support device to add additional functionality to the computer system.

The components provided in the computer system 700 of FIG. 7 are those typically found in computer systems that may be suitable for use with embodiments of the present disclosure and are intended to represent a broad category of such computer components that are well known in the art. Thus, the computer system 700 of FIG. 7 can be a PC, hand held computing system, telephone, mobile computing system, workstation, tablet, phablet, mobile phone, server, minicomputer, mainframe computer, or any other computing system. The computer may also include different bus configurations, networked platforms, multi-processor platforms, and the like. Various operating systems may be used including UNIX, LINUX, WINDOWS, MAC OS, PALM OS, ANDROID, IOS, QNX, and other suitable operating systems.

It is noteworthy that any hardware platform suitable for performing the processing described herein is suitable for use with the embodiments provided herein. Computer-readable storage media refer to any medium or media that participate in providing instructions to a CPU, a processor, a microcontroller, or the like. Such media may take forms including, but not limited to, non-volatile and volatile media such as optical or magnetic disks and dynamic memory, respectively. Common forms of computer-readable storage media include a floppy disk, a flexible disk, a hard disk, magnetic tape, any other magnetic storage medium, a Compact Disk Read Only Memory (CD-ROM) disk, DVD, BLU-RAY DISC (BD), any other optical storage medium, Random-Access Memory (RAM), Programmable Read-Only Memory (PROM), Erasable Programmable Read-Only Memory (EPROM), Electronically Erasable Programmable Read Only Memory (EEPROM), flash memory, and/or any other memory chip, module, or cartridge.

In some embodiments, the computer system 700 may be implemented as a cloud-based computing environment, such as a virtual machine operating within a computing cloud. In other embodiments, the computer system 700 may itself include a cloud-based computing environment, where the functionalities of the computer system 700 are executed in a distributed fashion. Thus, the computer system 700, when configured as a computing cloud, may include pluralities of computing devices in various forms, as will be described in greater detail below.

In general, a cloud-based computing environment is a resource that typically combines the computational power of a large grouping of processors (such as within web servers) and/or that combines the storage capacity of a large grouping of computer memories or storage devices. Systems that provide cloud-based resources may be utilized exclusively by their owners, or such systems may be accessible to outside users who deploy applications within the computing infrastructure to obtain the benefit of large computational or storage resources.

The cloud may be formed, for example, by a network of web servers that comprise a plurality of computing devices, such as the computer system 700, with each server (or at least a plurality thereof) providing processor and/or storage resources. These servers may manage workloads provided by multiple users (e.g., cloud resource customers or other users). Typically, each user places workload demands upon the cloud that vary in real-time, sometimes dramatically. The nature and extent of these variations typically depends on the type of business associated with the user.

While the present disclosure has been described in connection with a series of embodiments, these descriptions are not intended to limit the scope of the subject matter to the particular forms set forth herein. It will be further understood that the methods are not necessarily limited to the discrete components described. To the contrary, the present descriptions are intended to cover such alternatives, modifications, and equivalents as may be included within the spirit and scope of the subject matter as disclosed herein and defined by the appended claims and otherwise appreciated by one of ordinary skill in the art.

What is claimed is:

1. A computer-implemented method for providing an interactive discussion platform for a scientific research article, the method comprising:
   automatically crawling a website and extracting the scientific research article;
   executing instructions stored in a memory, wherein execution of the instructions by a processor:
      un-tars a direct dataset in a form of a tar file for the scientific research article and forms a tree-like structure;
      presents the scientific research article and the tree-like structure to an online resource;
      creates at least one public medium associated with the scientific research article, the at least one public medium automatically generated by a script;
      generates an interactive graphical user interface on a mobile client device, the interactive graphical user interface displaying the at least one public medium;
      receives, via the at least one public medium, at least one entry related to the scientific research article;
      displays the at least one entry via the at least one public medium;
      processes the at least one entry to determine a value of the scientific research article, the value associated with the scientific research article being provided to one or more users via the interactive graphical user interface of the mobile client device;
      extracts data from the scientific research article and the at least one entry;
      analyzes the data and actively learns at least one topic of interest based on the analyzed data;
      determines user popularity of the at least one topic of interest; and
      provides periodic updates to the one or more users via the interactive graphical user interface of the mobile client device, the periodic updates including one or more discussions in the at least one topic of interest;
      wherein the value of the scientific research article is based on one or more of an analysis of an interactive discussion, popularity of the scientific research article, evaluation of the scientific research article or marketing opportunities of the scientific research article.

2. The computer-implemented method of claim 1, wherein the at least one public medium includes a journal club and the at least one entry includes a video associated with the journal club.

3. The computer-implemented method of claim 1, wherein the at least one public medium includes a discussion forum and the at least one entry includes a comment associated with the discussion forum.

4. The computer-implemented method of claim 1, wherein the execution of the instructions by the processor further creates a social network including at least one social network member, the at least one entry being received from the at least one social network member.

5. The computer-implemented computer-implemented method of claim 4, wherein the at least one social network member includes one or more of a researcher, a peer of the researcher, an author, an editor, and a reviewer.

6. The computer-implemented method of claim 1, wherein the execution of the instructions by the processor further aggregates the at least one entry with one or more further entries associated with one or more further presented scientific research articles.

7. The computer-implemented method of claim 1, wherein the analyzing of the data includes a determination of trends in research with regard to the data.

8. The computer-implemented method of claim 1, wherein the the analyzing of the data includes one or more of natural language processing, manual analysis, keyword analysis, and big data analytics.

9. The computer-implemented method of claim 1, wherein the execution of the instructions by the processor further:
   based on the value, calculates a rating of the scientific research article in relation to other scientific research articles; and
   provides one or more scientific research articles based on the rating of each article.

10. The computer-implemented method of claim 9, wherein the execution of the instructions by the processor further:
    based on the rating, generates a message associated with the one or more scientific research articles; and
    sends the message to one or more client devices.

11. The computer-implemented method of claim 1, the interactive graphical user interface configured to dynamically display a specific, structured interactive graphical user interface paired with a prescribed functionality directly related to the interactive graphical user interface's structure.

12. A system for providing an interactive discussion platform for a scientific research article, the system comprising:
    at least one processor;
    a memory storing processor-executable instructions, wherein the at least one processor is configured to implement the following operations upon executing the processor-executable instructions:
       receive the scientific research article;
       present the scientific research article;
       create at least one public medium associated with the scientific research article;
       generate a graphical user interface via a client device, the graphical user interface displaying the at least one public medium;
       receive, via the at least one public medium, at least one entry related to the scientific research article;
       display the at least one entry via the at least one public medium;

processes the at least one entry to determine a value of the scientific research article, the value associated with the scientific research article being provided to one or more users via the graphical user interface of the client device;

extract data from the scientific research article and the at least one entry;

analyze the data and actively learn at least one topic of interest based on the analyzed data;

determine user popularity of the at least one topic of interest; and provide periodic updates to the one or more users via the graphical user interface of the client device, the periodic updates including one or more discussions in the at least one topic of interest; and a database in communication with the at least one processor and configured to store at least the scientific research article and the at least one entry; wherein the value of the scientific research article is based on one or more of an analysis of an interactive discussion, popularity of the scientific research article, evaluation of the scientific research article or marketing opportunities of the scientific research article.

13. The system of claim 12, wherein the at least one public medium comprises a journal club and the at least one entry includes a video associated with the journal club.

14. The system of claim 13, wherein the video includes a live video conference associated with the scientific research article.

15. The system of claim 12, wherein the at least one public medium comprises a discussion forum and the at least one entry includes a comment associated with the discussion forum.

16. The system of claim 12, wherein the at least one public medium comprises an online poll related to the scientific research article and the at least one entry includes a poll answer.

17. The system of claim 12, wherein the scientific research article is assigned a category based on natural language processing, manual analysis, and keyword analysis of content of the scientific research article.

18. The system of claim 12, wherein the scientific research article is associated with a printed article, wherein the printed article comprises a link to the public medium, the link being one or more of the following: a web address and a quick response (QR) code.

19. The system of claim 12, wherein the at least one processor is further configured to implement an operation of:
upon receiving the at least one entry, send a notification to an author of the scientific research article.

20. The system of claim 12, wherein the at least one processor is further configured to implement operations of:
based on the value, calculate a rating of the scientific research article in relation to other scientific research articles;
provide one or more scientific research articles in accordance with the rating of each article;
based on the rating, generate a message associated with the one or more scientific research articles; and
send the message to one or more users.

21. The system of claim 12, wherein the database is further configured to store raw data submitted by a user of the interactive discussion platform.

22. A non-transitory computer-readable medium comprising instructions, which when executed by one or more processors, perform the following operations:
receive, by an interactive discussion platform, a scientific research article, the interactive discussion platform coupled to a server and executable by the one or more processors;
present the scientific research article;
create at least one public medium associated with the scientific research article;
generate a graphical user interface via a client device;
receive at least one entry related to the scientific research article;
display the at least one entry via the at least one public medium;
process the at least one entry to determine a value of the scientific research article, the value associated with the scientific research article being provided to one or more users via the graphical user interface of the client device;
extract data from the scientific research article and the at least one entry;
analyze the data and
actively learn at least one topic of interest based on the analyzed data;
determine user popularity of the at least one topic of interest; and
provide periodic updates to the one or more users via the graphical user interface of the client device, the periodic updates including one or more discussions in the at least one topic of interest; wherein the value of the scientific research article is based on one or more of a number of users reading or discussing the scientific research article, number of users commenting on the scientific research article, or ranking of the scientific research article.

* * * * *

UNITED STATES PATENT AND TRADEMARK OFFICE
CERTIFICATE OF CORRECTION

PATENT NO. : 10,269,457 B2
APPLICATION NO. : 14/251477
DATED : April 23, 2019
INVENTOR(S) : Steven F. Palter It is certified that error appears in the above-identified patent and that said Letters Patent is hereby corrected as shown below:

In the Claims

In Claim 5, Column 14, Line 14 and 15, the text currently reads:
-The computer-implemented computer-implemented method of claim 4-,
It should read:
--The computer-implemented method of claim 4--.

In Claim 8, Column 14, Line 27, the text currently reads:
-wherein the the analyzing of the data includes one or more-,
It should read:
--wherein the analyzing of the data includes one or more--.

Signed and Sealed this
Seventeenth Day of September, 2019

Andrei Iancu
*Director of the United States Patent and Trademark Office*